United States Patent [19]

Kelly

[11] Patent Number: 4,856,499

[45] Date of Patent: Aug. 15, 1989

[54] ERECTION DEVICE

[75] Inventor: Edward C. Kelly, Blue Bell, Pa.

[73] Assignee: Assist Research Corp., Hatfield, Pa.

[21] Appl. No.: 180,010

[22] Filed: Apr. 11, 1988

[51] Int. Cl.$^4$ ............................................. A61F 5/41
[52] U.S. Cl. ..................................................... 128/79
[58] Field of Search .......................... 128/79, 38, 327; 604/346; 119/14.52; 251/5

[56] References Cited

U.S. PATENT DOCUMENTS

| | | | |
|---|---|---|---|
| 2,581,114 | 1/1952 | Larson | 128/79 |
| 2,874,698 | 2/1959 | Sell | 128/79 |
| 3,744,486 | 7/1973 | Wilson | 128/79 |
| 3,773,040 | 11/1973 | Gavrilovich | 128/79 |
| 4,102,335 | 7/1978 | Woodward et al. | 128/79 |
| 4,139,007 | 2/1979 | Diamond | 128/79 |
| 4,224,933 | 9/1980 | Reiling | 128/79 |
| 4,684,364 | 8/1987 | Sawyer et al. | 251/5 |
| 4,718,411 | 1/1988 | Stewart | 128/79 |
| 4,741,329 | 5/1988 | Marcune | 128/79 |

*Primary Examiner*—Robert Peshock
*Assistant Examiner*—Cary E. Stone
*Attorney, Agent, or Firm*—Gregory J. Gore

[57] ABSTRACT

A medical erection device to treat impotency in men provides a detachable pump portion and a safety valve to prevent over-depressurization. Cooperating guide rails permit the pump portion to be detachable from the vacuum cylinder. The pump has an extremely short stroke and is operated by a handle parallel to the axis of the vacuum cylinder to provide for easy, one-handed operation. A constrictor ring is provided to inhibit the return flow of blood from the penis to sustain the erection once achieved.

13 Claims, 7 Drawing Sheets

ERECTION DEVICE

FIELD OF THE INVENTION

This invention relates to a surgical device to help promote an erection of the male penis. This device includes a vacuum chamber which, in practice, is fitted over the penis to induce the flow of blood into the genital organ and thereby cause an erection.

SUMMARY OF THE PRIOR ART

Sexual impotence in men has been recognized as a serious medical dysfunction over the centuries. Increasing scientific knowledge has led to greater understanding of the male erection process which is caused by the flow of blood to the corpora cavernosa tissues of the penis. With this understanding came the invention of devices to induce and control the blood flow in order to cause and maintain an erection to overcome the dysfunction.

In 1917, U.S. Pat. No. 1,225,341 issued to Dr. Otto Lederer for a surgical device included a vacuum chamber connected to a suction bulb for creating a vacuum. The vacuum created by this device is limited only by the capability of the suction bulb.

Over the next 50 years, various improvements have been made to this simple design. U.S. Pat. No. 3,631,853 to Marvin A. Burdette which issued in 1972 includes a piston-type pump for creating higher vacuums. The piston-type pump of this invention is fitted with a long interconnecting tube which travels between a piston pump and a vacuum chamber in order that the pump can be operated from a remote location. In this device, a maximum vacuum limit is controlled by the pressure of a spring assembly against the vacuum pump piston.

A further development was contributed by Eldon M. Wilson described in U.S. Pat. No. 3,744,486 which issued in 1973. This apparatus discloses the location of a piston pump assembly affixed to the vacuum chamber and actuated by a hand lever. The device included a frusto-conical shaped entrance to the vacuum chamber in order to facilitate removal of the penis after enlargement. However, this device contains no safety feature for limiting the extent of vacuum and requires two hands to operate.

An area of function which has not been adequately addressed is effective means for limiting the vacuum created in the vacuum chamber and also the capability to adjust this vacuum limit among users. Injury may be caused by rupturing blood vessels if too much vacuum is created around the penis. Furthermore, different patients require different vacuum levels to accommodate different degrees of dysfunction. In addition, there is a need for an erection-stimulating device which is more convenient to use and that can be operated only with one hand. This is particularly important in situations of paralysis or amputation where the patient does not have the use of both hands.

Another problem with using the prior art devices is the ring-like structure which is often employed to act as a tourniquet about the base of the penis to prevent the blood from returning from the penis prematurely. By the use of this constrictor ring, the erection can be maintained for longer periods. Most often, however, these rings have been simple rubber bands which are difficult to handle and are not properly sized to accommodate penises of varying diameter.

U.S. Pat. No. 4,203,432 discloses an improved ring for maintaining an erection. This improved constrictor ring only contacts the surface of the penis partially and constrictive force is applied by a rubber band stretched between the two free ends of the open ring. While this device may have shown an improvement over the prior art for its adjustability, it is still difficult to use in that it requires a certain amount of dexterity to manipulate the rubber bands. It is particularly a problem with the physically impaired and elderly who often are the type of patients most needy of a therapeutic erection device.

It is therefore an object of the present invention to create an erection stimulating device which is both safe and easy to use. It is a further object of the present invention to include improved constrictive rings for maintaining the amount of blood in an erect penis which requires a minimal amount of manual dexterity and which is simple and safe to use. Other objects and advantages of the present invention will become apparent to those of ordinary skill in the art from the drawings and further description presented herein.

SUMMARY OF THE INVENTION

In order to achieve the objects and overcome the deficiencies with prior art devices described above, the applicant has devised an erection device which provides simple, one-handed operation and further includes a vacuum-limiting safety feature to prevent injury. The present invention utilizes a horizontally disposed piston-type pump which has a very short stroke actuated by a simple elongate lever parallel to the vacuum chamber sleeve. Because of the orientation and stroke of the lever, the pump mechanism may be worked by individual fingers of one hand, while the remaining fingers maintain suitable grasp of the device. This permits convenient, one-handed operation.

In one embodiment of the present invention, the pump assembly may be detachably affixed to the vacuum chamber so that when detached and connected with an extra length of tubing, the pump assembly may be easily worked from a remote location. This feature provides two operational attributes in one device.

The present device further includes a pressure-limiting safety feature which includes a collapsible length of tubing interconnecting the pump cylinder and vacuum chamber. The pressurization point of collapse of this tubing is selected to coincide with a maximum safe vacuum limit. In this way, the pump device becomes self-regulating. Air flow is stopped between the pump and the vacuum sleeve when the maximum safe vacuum limit is exceeded.

The present device also includes constrictor rings for use in maintaining the erection which have individual accommodation, but are very controllable and easy to use because they are relatively inelastic and hold their shape. The use of a rigid material means that the ring structure is easy to handle. Novel attachment means permits the ring to be easily fastened in place. In one embodiment, fastening the free ends of the ring is provided by the frictional linking capabilities of a material, such as Velcro ®.

DESCRIPTION OF THE PREFERRED EMBODIMENT

Figure 1:
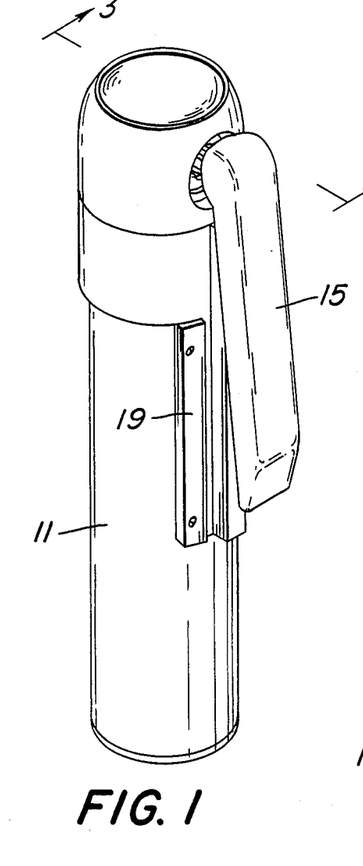
FIG. 1 is a top perspective view.
Figure 2:
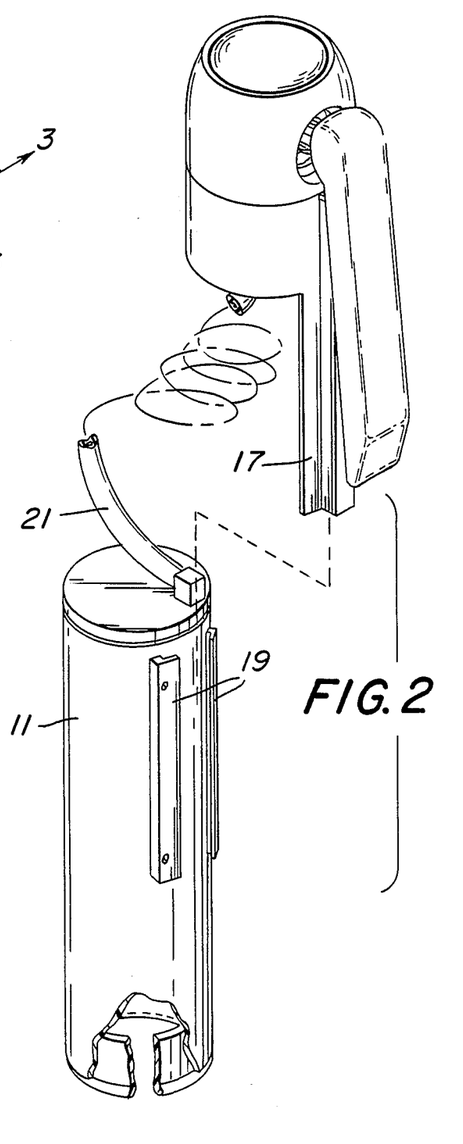
FIG. 2 is a top perspective view showing the detachable nature of the pump portion.

FIGS. 1 and 2 show the general features of the present invention. One of the novel aspects is the conveniently detachable pump portion 13 which is fitted atop the tranparent vacuum chamber sleeve 11. These two elements are fitted together by the cooperation between slide member 17 connected to the pump portion and guide rails 19 secured circumference of the vacuum chamber sleeve. In its detached state, a substitute elongate air hose 21 is added to span the distance from the pump portion which may be held at a remote location from the vacuum chamber sleeve. Pump handle 15 works the pump piston and has a very short stroke to permit simple, one-handed operation.

Figure 3:
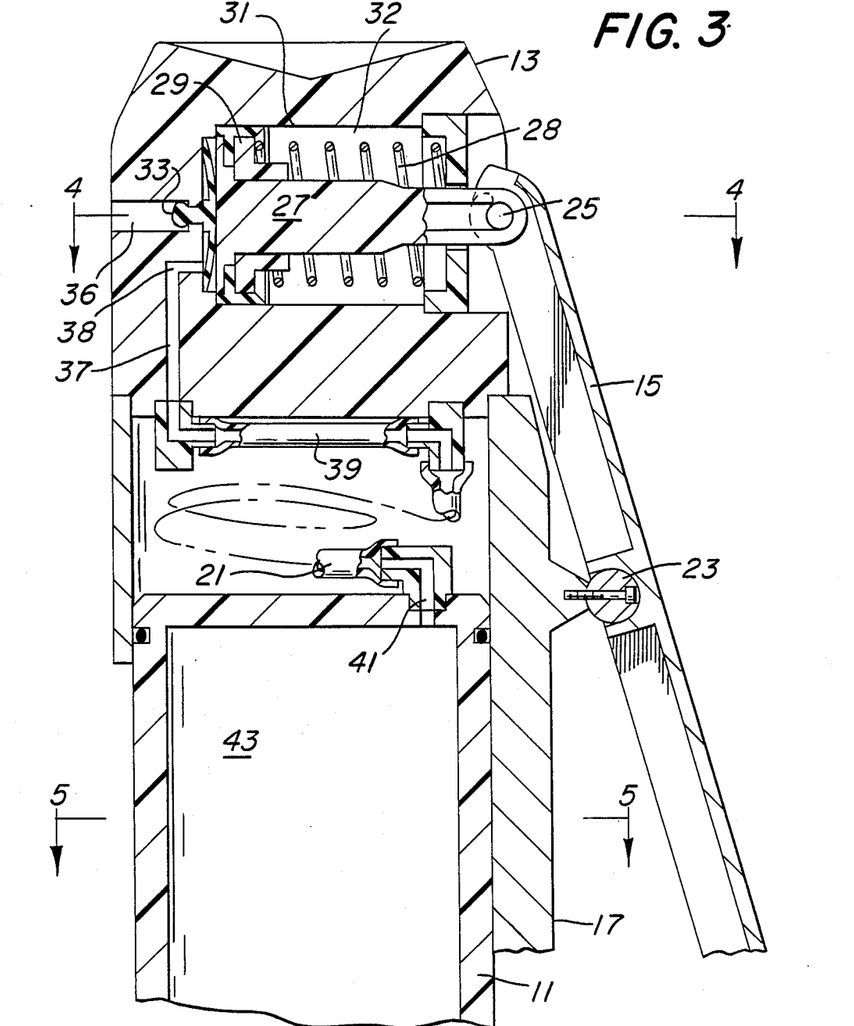
FIG. 3 is a side sectional view of FIG. 1 showing details of the pump and lever-actuating mechanism.

FIG. 3 is a sectional view showing the details of the working components of the vacuum pump. Handle 15 is a simple lever having a fulcrum established by fulcrum barrel 23. The actuating end of the handle lever cooperates with pivot pin 25 to reciprocate piston rod 27. Piston rod 27 carries piston 29 which includes a sealing piston ring 31 which rides against the wall of pump cylinder 32. Spring 37 biases the piston in the down position and holds the bottom handle end of the lever away from the outer wall of the vacuum chamber sleeve at rest. Hence, the piston may be controllably reciprocated by squeezing the lower handle end of the lever 15 in the direction of the sleeve chamber outer wall with one hand.

A double check valve 33 regulates the flow of air into and out of the pump cylinder 32. A vacuum is created in chamber 43 within vacuum sleeve 11 by removing air therein through vacuum chamber exhaust port 41. The vacuum chamber exhaust port 41 is in fluid communication with pump intake air port 37 through air hose 21 and collapsible safety valve 39. Double check valve 33 works to close exhaust port 35 and exhaust port valve 36 when the piston moves off its seat creating a vacuum within the pump cylinder 32. Simultaneously, air intake flap valve 38 opens under this condition allowing air to flow from the vacuum chamber into the piston cylinder. As the piston is released and it moves back to its rest position by spring 37, the air inside the pump cylinder is compressed which simultaneously closes the air intake port and opens exhaust port valve 36, thereby expelling air out of the pump cylinder through exhaust port 35. By these relations, it will be understood by one of ordinary skill in the art that the pump mechanism will remove air from the vacuum chamber and expel it into the atmosphere.

Collapsible tubing member 39 is made of relatively elastic material which has been selected to collapse when a predetermined vacuum of a maximum value is exceeded. This structure is fitted between ports 55 and 57 which hold the tubing without any bending so that it forms a straight cylinder. This permits the collapsibility to be predictable and repeatable. This structure acts as a cylindrical diaphragm which constricts when outside pressure is sufficiently greater than the interior pressure and closes to limit the vacuum created in chamber 43. This piece of elastic tubing is readily accessible with the pump portion detached and is easily replaced with a member of different elasticity in order to vary the maximum vacuum set point. Tubing 39 therefore not only acts as a safety valve, but also as a convenient means of vacuum adjustability through simple exchange of parts.

Figure 4:
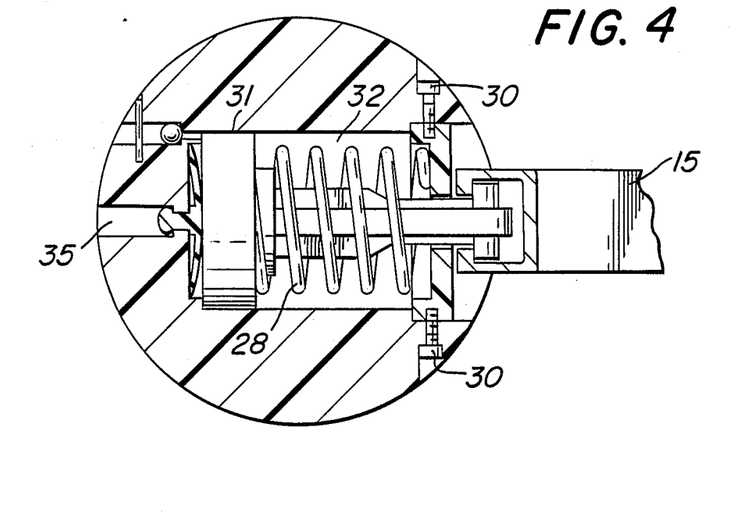
FIG. 4 is a top sectional view of the pump piston and valve assembly.

Referring now to FIG. 4, further detail of the pump mechanism is depicted. Handle member 15 cooperates with pivot pin 25 slideably to permit straight line movement of piston rod 27 while maintaining the angular swing of handle 15. The pump assembly includes a side plate 30 which includes a central hole for passage of the piston rod 27. Top plate 30 is conveniently retained by screw means 30. Since the cylinder 32 is intended to be pressurized on the top plate side of the piston, no sealing is required. Spring means 28 resiliently bias the piston so that the pump cylinder is completly exhausted at rest. Cylinder 32 is formed within the main body of the pump portion 13. Piston ring 31 provides the proper seal to create the required pressure fluctuations to opposite side of the piston.

Figure 5:
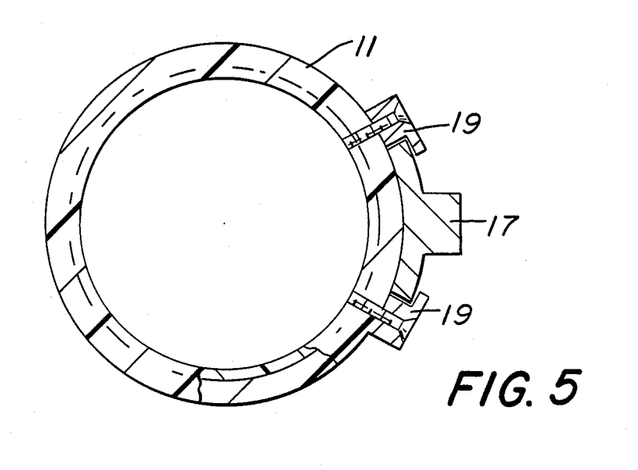
FIG. 5 is a top sectional view of the vacuum chamber sleeve showing the releasable fastening means interconnecting the vacuum chamber sleeve and the pump assembly.

Referring now to FIG. 5, guide rails 19 are affixed to the outer wall of vacuum chamber sleeve 11 by way of simple screw means. Guide rails 19 are L-shaped elongate members which slidably affix elongate member 17 which is rigidly affixed to the pump portion. By way of cooperation between these elements, the pump portion may be made conveniently detachable from the vacuum chamber sleeve. Vacuum chamber sleeve 11 is preferably made from a transparent plastic material so that the progress and degree of erection during the operation of the device can be observed.

Figures 6, 7, 8, 9, 10:
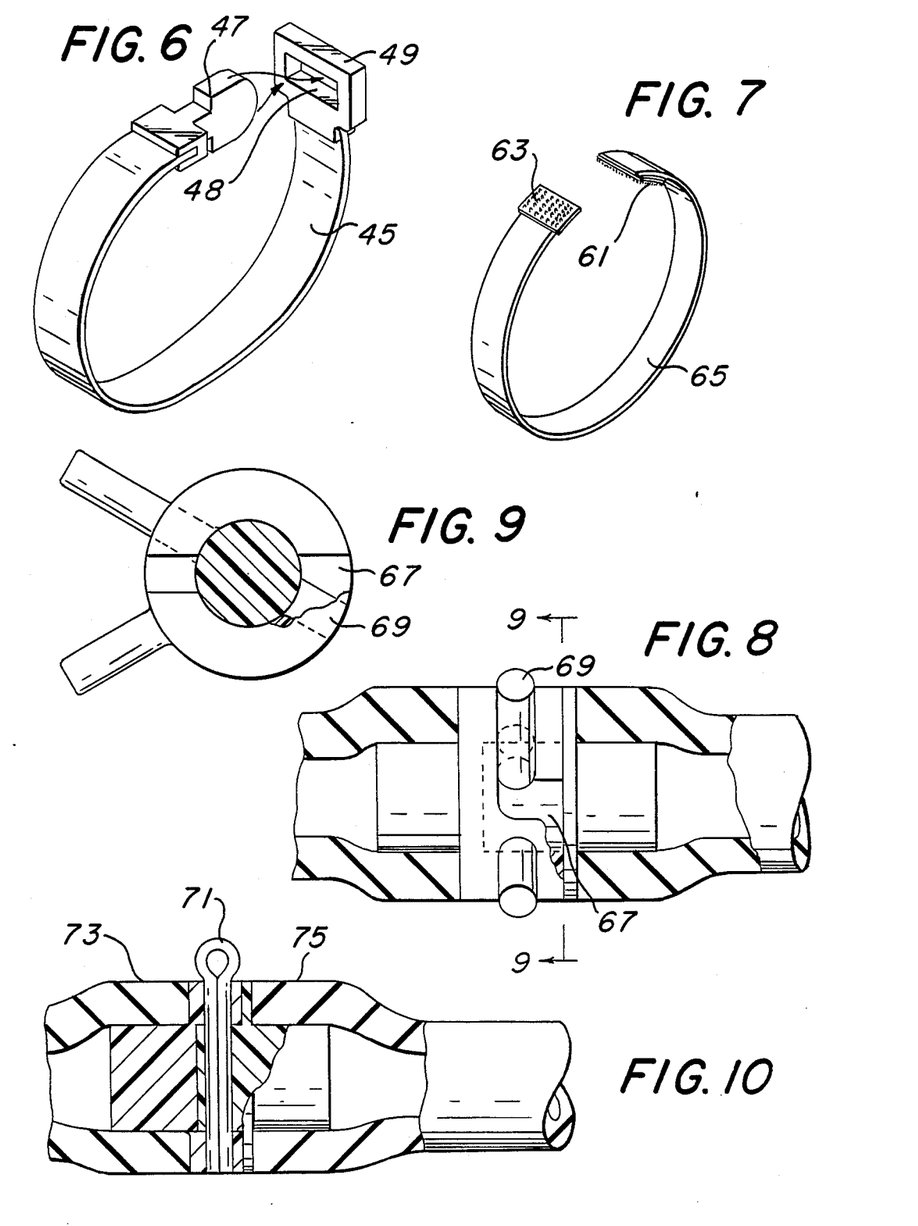
FIGS. 6 and 7 are perspective views alternate embodiments of constrictor rings.
FIGS. 8 through 14 show sectional views of various embodiments of splice connectors for joining the ends of the constrictor ring.

As discussed above, constrictor rings are often used in association with a vacuum erector device. As disclosed herein, a constrictor ring of increased convenience and effectiveness has been achieved. FIG. 6 shows a constrictor ring which is formed of securing ends of strap 45 by splice means 47 and 49 to form a key and eye interconnection to effect closure of the ring. Key hook 47 is made of elastomeric material which is torsionally deformable and can be rotated approximately 90 degrees with respect to its normal resiliently biased vertical orientation. This member can be twisted and inserted through horizontal opening 48 and then released. It will be readily understood that this will effect secure closure of the ring.

Adjustability of ring size is achieved through replacement of parts. The patient selects from a plurality of straps of different lengths in order to achieve the proper fit. Except for hook member 47, the remainder of strap 45 is constructed of relatively inelastic material. This reduces the manual dexterity needed to operate the constrictor ring.

FIG. 7 shows a constrictor ring which is similarly formed by closing the ends of strap 65. In this embodiment, closure is effected by Velcro ® portions 63 and 61.

Figure 11:
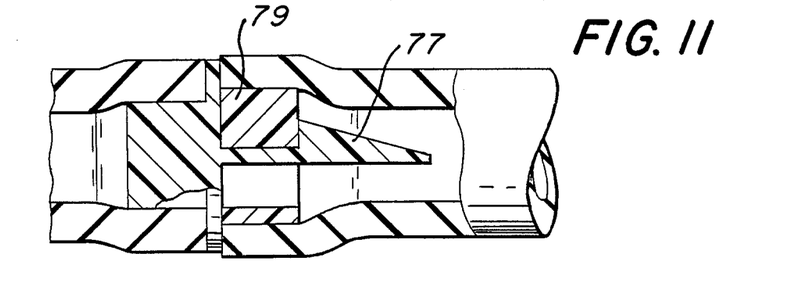
Figure 12:
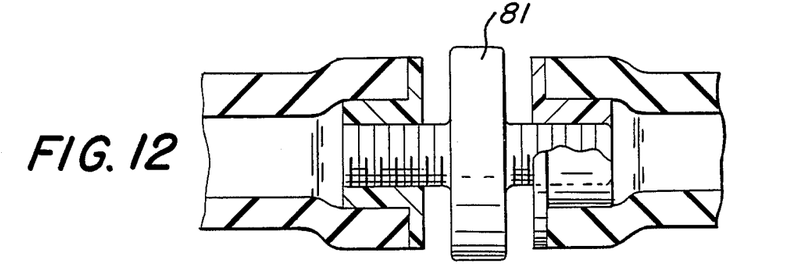
Figure 13:
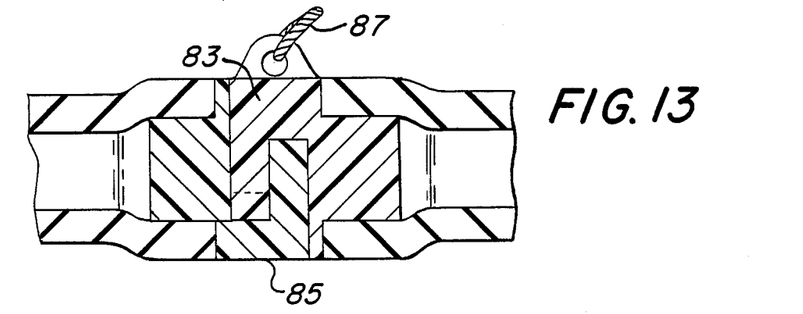
Figure 14:
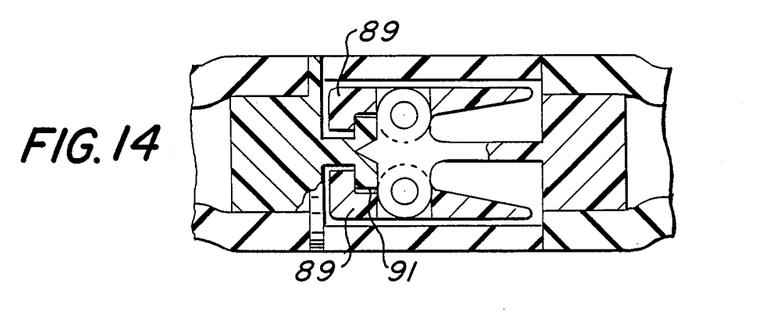

FIGS. 8 through 14 show sectional views of the various alternate embodiments which accomplish the loop closure function of the constrictor ring. FIGS. 8 and 9 show a different form of axial twist connector. Connector arm 69 is received within lateral L-slot 69. FIG. 10 shows a releasable pin 71 which is received within a lateral bore through cooperating male and female elements 73 and 75. FIG. 11 shows a snap connector within wedge-shaped snap head 77 is received between resilient jaws 79. FIG. 12 shows a threaded turnbuckle-type connector wherein bolt element 81 may be rotated for precise length adjustment. FIG. 13 shows and S-type snap connector having interlocking jaw members 83 and 85, and further including a pull cord 87 for quick release. FIG. 14 shows a clamp connector having resilient opposing jaws 89 which clamp behind T-shaped head 91.

FIGS. 15-19 show an alternate embodiment of the present invention wherein the piston and cylinder are oriented in line with the axis of the erection device cylinder. It will be readily understood to those of skill in the mechanical arts the basic functioning of the pump mechanism shown in these figures. The operation is similar to the embodiment in FIGS. 3 and 4, except with different pump cylinder valving. In this embodiment, ball check valves 57 and 59 ensure the one-way movement of air from intake port 51 out through exhaust port 53 by reciprocation of the pump handle. As with the transverse piston embodiment, flexible tube means 54 represents a conduit in series with the air flow path indicated by the arrows 55 in FIG. 15. Tube means 54 serves the same function and purpose as air hose 21 previously described and shown in FIGS. 2 and 3.

Figure 15:
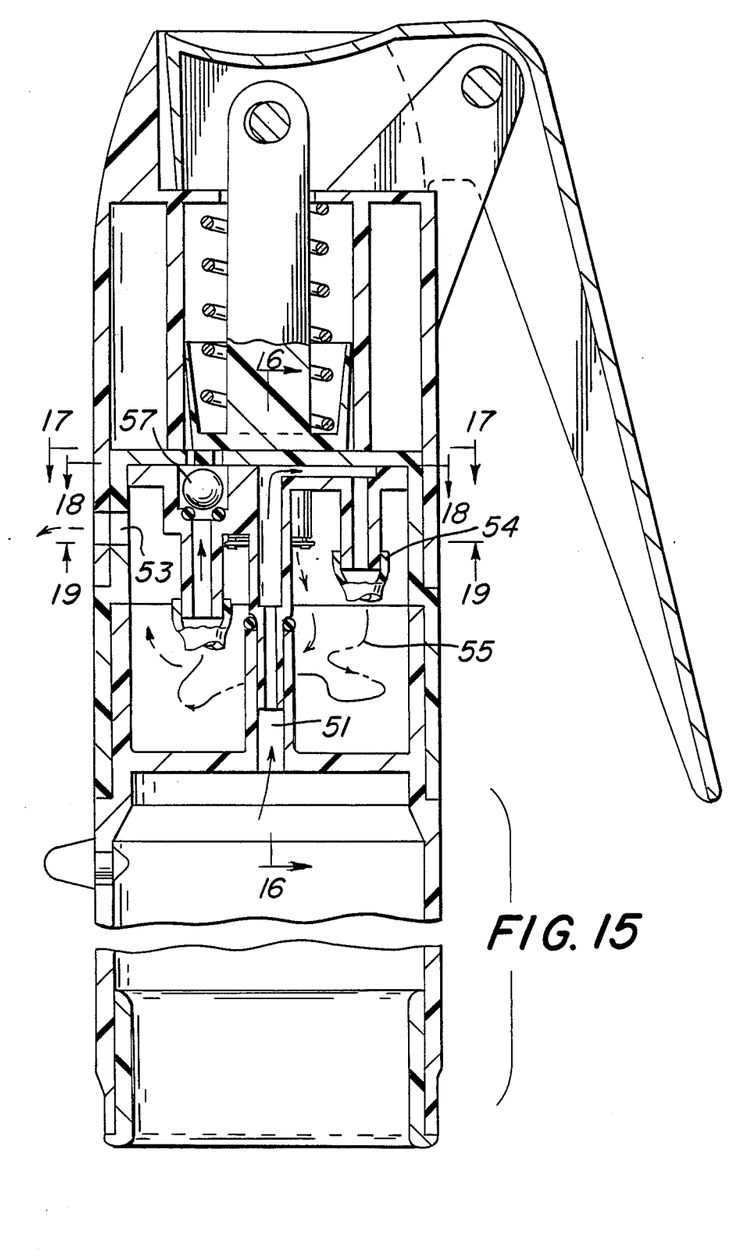
FIG. 15 shows a sectional view of an alternate embodiment wherein the piston pump and cylinder are oriented in line with the central axis of the erection device.
Figures 16, 17, 18, 19:
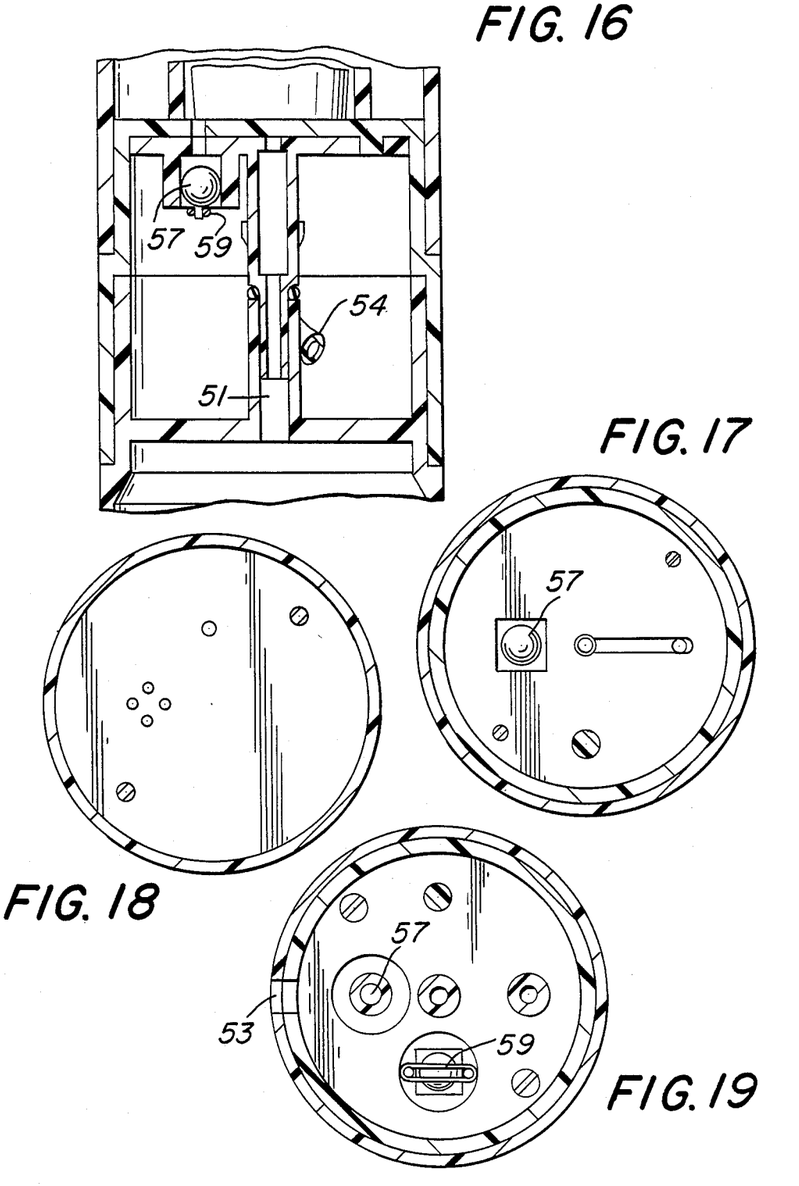
FIG. 16 is a side sectional view taken from FIG. 15.
FIG. 17 is a top sectional view taken from FIG. 15.
FIG. 18 is a top sectional view taken from FIG. 15.
FIG. 19 is a bottom sectional view taken from FIG. 15.

FIGS. 17, 18 and 19 are sectional views taken from FIG. 15 as indicated in that figure. These figures show greater detail of the air porting and ball check valves 57 and 59.

OPERATION

The operation of either embodiment of the present erection device is very straightforward and simple. The transparent vacuum chamber sleeve 11 is fitted around the penis so that the circular end of the sleeve is in contacting relationship with the person's body around the root of the penis. This contact provides a sufficient seal against vacuum which because of the softness of the tissues in that area tend to increase the seal as higher vacuums are achieved. With the vacuum chamber sleeve so fitted, the pump handle is then reciprocated either with the pump portion remaining attached to the vacuum sleeve chamber or with it detached and operated from a remote location. As higher vacuums are achieved by manipulating the pump handle, the progress of the erection is visually monitored by the operator. As soon as sufficient erection is achieved, vacuum is released from the vacuum chamber's sleeve and it is then removed from around the penis. The appropriate constrictor ring is then placed around the root of the penis in order to prevent the return flow of blood and thereby maintain the erection. Sexual intercourse may now be performed in the usual manner and thereafter the constrictor ring removed returning the penis to its normal flaccid state.

It should be understood that the above description discloses specific embodiments of the present invention and are for purposes of illustration only. There may only be other modifications and changes obvious to those of ordinary skill in the art which fall within the scope of the present invention which should be limited only by the following claims and their legal equivalents.

What is claimed is:

1. A medical device for promoting an erection in the male genital organ, including a vacuum chamber, comprising:
   a. a pump having a reciprocating piston moving within a cylinder and including an intake port and an exhaust port;
   b. an elongate transparent cylindrical vacuum chamber releasably attached to said pump, said pump affixed to a first end of said cylindrical vacuum chamber and a second opposite end of said chamber having an opening for receiving the male penis, said pump having an actuation handle which is substantially parallel to said elongate vacuum chamber; and
   c. air conduit means in fluid communication with said vacuum chamber and said pump, said air conduit means further including a safety valve being a portion of said air conduit means comprising a substantially straight elastomeric cylinder which is supported at opposite ends by two rigid port means affixed to a common support structure.

2. The medical device of claim 1 further including a elongate slide portion and two (2) guide rails, said elongate slide portion being affixed to said pump and said guide rails being affixed to the outer wall of said elongate cylindrical vacuum chamber, said slide member and said hand rails being axially engageable permitting said pump to be detachable from said vacuum chamber.

3. The medical device of claim 2 further including resilient means located within the cylinder of said pump to bias the pump piston to a rest position where said pump cylinder is exhausted.

4. The medical device of claim 3 further including a double-check valve movable in opposite directions, said valve simultaneously opening the pump cylinder intake port and closing the pump cylinder exhaust port when moved in one direction, and simultaneously opening the pump cylinder intake port and closing the cylinder exhaust port when moved in the opposite direction.

5. The medical device of claim 4 further described in that said pump, piston, and cylinder are oriented transverse to the axis of said elongate cylindrical vacuum chamber.

6. The medical device of claim 5 and a constrictor ring fitted around the base of the penis after an erection has been attained.

7. The medical device of claim 6 wherein said constrictor ring comprises a strap portion of relatively inelastic material and a closure device having two separate portions, each portion attached to opposite ends of said strap.

8. The medical device of claim 7 further described in that said closure device comprises a key and eye hook, said key being resiliently torsional having a rest position wherein of said key is perpendicular to a slot in the eye portion.

9. The medical device of claim 7 further described in that said closure device of said constrictor ring includes two pieces of Velcro ® material attached to the ends of said strap portion.

10. The medical device of claim 7 further including a pin releasably engageable through both portions of said closure device.

11. The medical device of claim 7 further described in that said closure device further includes an axially disposed threaded member having an enlarged portion approximately in the center thereof, said threaded member being threadably engageable with cooperating apertures in both portions of said closure device.

12. The medical device of claim 7 further described in that said closure device includes a pair of resiliently biased opposing jaw members in one portion and a tab with an enlarged head affixed to the other closure portion, said head being dimensioned to fill the space between the said jaws at rest.

13. The medical device of claim 4 further described in that said pump, piston, and cylinder are oriented in line with the axis of said elongate cylindrical vacuum chamber.

* * * * *